United States Patent [19]

Miller

[11] 4,028,730

[45] June 7, 1977

[54] VIDICON CAMERA FOR CLOSED CIRCUIT TELEVISION SYSTEM

[75] Inventor: Frederick A. Miller, Santa Barbara, Calif.

[73] Assignee: Circon Corporation, Santa Barbara, Calif.

[22] Filed: May 17, 1976

[21] Appl. No.: 687,314

[52] U.S. Cl. .............................. 358/217; 358/229
[51] Int. Cl.² ......................................... H04N 3/16
[58] Field of Search ............. 358/93, 98, 100, 217, 358/229, 209, 44; 178/DIG. 27, DIG. 1; 313/365; 315/3

[56] References Cited

UNITED STATES PATENTS 3,114,799  12/1963  Waters et al. ..................... 358/100

Primary Examiner—John C. Martin
Attorney, Agent, or Firm—Daniel J. Meaney, Jr.

[57] ABSTRACT

A vidicon camera adapted for use in a direct wire television system and having a vidicon tube, a metal housing having means defining an opening therethrough to permit an optical image to be focused on the imaging surface of the vidicon tube, a first printed circuit board having an aperture of sufficient size to permit the optical image to pass therethrough positioned in the housing between the housing opening and the imaging surface of the vidicon tube wherein the first printed circuit board including preamplifier means electrically connected to the vidicon tube for receiving composite video signals and producing amplified in-phase adapted composite video signals, a second printed circuit board positioned between the end of the vidicon tube opposite the end having the imaging surface and the housing, wherein the second printed circuit board includes amplifier means for amplifying in-phase the composite video signals with a predetermined gain, emitter follower amplifying means electrically connected to the amplifier means and adapted to drive a direct wire with the amplified composite video signal and conductor means electrically connected between the vidicon tube, the first and second printed circuit boards and a remote television system is shown.

17 Claims, 5 Drawing Figures

VIDICON CAMERA FOR CLOSED CIRCUIT TELEVISION SYSTEM

BACKGROUND OF THE INVENTION

1. Field of Invention

This invention relates to a vidicon camera adapted for use in a closed circuit television system and in particular a small, compact vidicon camera mounted in a housing adapted to be connected by a coaxial cable to a remote television system. The vidicon camera is remotely located from the video processor and other components of a closed circuit television system. The present invention has utility for use in a television microscope system wherein the video camera is attached directly to a microscope. A microscope may be used for viewing small articles or a selected small field of vision such as in a medical operation. The microscope produces an optical image which is directed onto the imaging surface of the vidicon camera by a lens system. The vidicon camera converts the optical image into a composite video signal having chrominance signals representative of the optical image. The composite video signal is used in a closed circuit or direct wire television system for producing a colored television picture which is representative of the optical image being viewed by the microscope.

2. Description of the Prior Art

Small compact video cameras adapted for use in a direct wire television system are known in the art. In one known vidicon camera, camera housing encloses a vidicon tube, horizontal and vertical deflecting coils, focusing controls, filters, preamplifier and amplifier and a video processor. The output of the video camera is an amplified processed composite video signal capable of being applied directly to a television monitor, television receiver or video recorder. In such a device, the video camera is of fairly large size in order to enclose all of the components as described above. The size of such a video camera is large relative to the size of a microscope. Because of the size of such video cameras, it is cumbersome to attach, connect or otherwise position a video camera relative to a microscope or other similar instrument to receive the optical image.

Another disadvantage of a known prior art is that the video camera normally includes a video processor which functions to produce a composite video signal which is adapted to be directly applied as an input to a television monitor, television receiver, or video recorder. In addition, integral with the video camera are the electronics and controls for controlling horizontal and vertical deflection coils and the focusing coils. The inclusion of a video processor, video processor electronics and control electronics for the horizontal and deflection coils and focusing coils results in increased size and weight of the camera.

It is also known in the art to separate the video processor from the video camera head and to interconnect the same with direct wire, coaxial cable or other similar electrical connecting means. In such devices, the video camera head is still relatively large size for ease of use with certain applications. Such known video cameras generally have deflection circuits and other control circuitry within the camera housing thereby imposing a limit on how small the housing can be to enclose the camera components.

The ease and the ability to use a video camera in connection with laboratory or medical instruments which generate an optical image are limited directly by the size and weight of such a video camera. For example, an endoscope may be used for exploring the interior of a human body. An optical image representing the small field of view is displayed by means of a lens system in a viewer. A physician observes, through the viewer, the small interior area of the body viewed by the endoscope. By attaching or connecting a video camera to the endoscope, the optical image can be displayed in a television monitor or recorded on a video recorder.

Another disadvantage of the presently known video cameras is that a relatively large electrically connecting cord is required between the video camera and the television system for displaying the television image picked up by the video camera. The large electrical connecting cable becomes difficult to maneuver and has a limited degree of flexibility in an operating room or laboratory experiment.

In addition to medical application, there are numerous other applications which utilize video cameras for viewing images through microscopes. Such applications include assembly and wiring of integrated circits, assembly of precision electronic compoqents and for making measurements of microscopic objects. In such applications, it is desirable to display and/or record a video representation of the optical image for a number of purposes. One purpose is to reduce or elminiate eye fatigue of an observer or technician performing the examination and/or test work. In such applications, the size of the video camera limits the practicability and the type of environment in which such a television microscope system can be used.

There are large number of presently known closed circuit television systems wherein a video camera is remote from the television receiver, television monitor or video recorder wherein the video camera is used to utilize optical images developed from a variety of instruments. In such applications it is highly desirable to have the actual pick up video camera head be as small, compact and light weight as possible. The presently known video cameras generally have a weight in the order of 3 lbs. (1.36 kg) or more and have dimensions which are in the order of approximately 6 inches (15.4 cm) in length, 6 inches (15.4 cm) in height and 4 inches (10.26cm) in width and enclose substantially all the electronics and controls necessary to enable the video camera to operate as a separate independent device.

SUMMARY OF THE INVENTION

The present invention overcomes several disadvantages of the known prior art video cameras adapted for use in a closed circuit or direct wired television system. One advantage of the present invention is that the video pick-up device or video camera head is essentially a vidicon camera. The vidicon camera includes the minimum number of elements to generate and transmit a composite video signal with chrominance signals which are, in turn, received and processed remotely. The width and size of the compact vidicon camera is substantially less than that of known video cameras used in closed circuit or direct wire television systems.

Another advantage of the present invention is that the small compact, lightweight, color vidicon camera is capable of being connected to or attached to an optical microscope, endoscope, or other instrument or apparatus which produces an optical image to be viewed by a user. In one known application, the vidicon camera of the present invention can be used for viewing a medical surgical operation.

A microscope is utilized by a surgeon to view and observe a limited area of a human body which is being operated upon by the surgeon. The optical image developed by the microscope is transmitted through a beam splitter producing an image which is directed to an eye piece or viewer to enable a surgeon who is performing the operation to directly view the operation. The second beam or optical image is directed to a lens system which focuses an optical image on the imaging surface of the color vidicon camera. Due to the small size and weight of the color vidicon camera, the camera is attached to and supported by the microscope without the need of external medical support. A single user can operate the microscope and perform the operation.

Another advantage of the vidicon camera of the present invention is that the vidicon camera encloses the vidicon tube, the horizontal and vertical deflection coils, the focusing coils and two small printed circuit boards. The output signal from the vidicon camera is a low level composite video signal having chrominance signals therein which represents the optical image focused on the imaging surface of the vidicon tube. The low level composite video signal is capable of being terminated by a coaxial cable to a remote video processor. The video processor then amplifies and processes the composite video signal including insertion of appropriate vertical and horizontal blanking signals, synchronizing signals and clamping signals. The output of the remote video processor is a so-called processed composite video signal having an amplitude and frequency of meeting the input requirements of standard television monitors, television receivers or video recorders. Control circuitry for the vertical and horizontal deflection coils in the video camera and the control circuitry for the focusing coil are likewise located remotely to the video camera. Thus, the horizontal and vertical deflection signals are generated remotely and applied via conductors to the vidicon camera. By using the techniques of the present invention a small, compact color vidicon camera having a size in the order of 8 inches (20.52cm) in length, 2 inches (5.12 cm) in width and 2 inches (5.12 cm) in depth and a weight in the order of 1.5 lbs (0.68 kg) can be fabricated. The small, compact, lightweight vidicon camera has wide utility in a number of applications wherein the camera is coupled directly to an apparatus producing an optical image or adapted to have an optical image focused thereon by means of a lens system.

BRIEF DESCRIPTION OF THE DRAWING

The foregoing and other advantages and features of the invention will be apparent from the following description of the preferred embodiment of the invention when considered with the illustrations in the accompanying drawing which includes the following figures.

Figure 1:
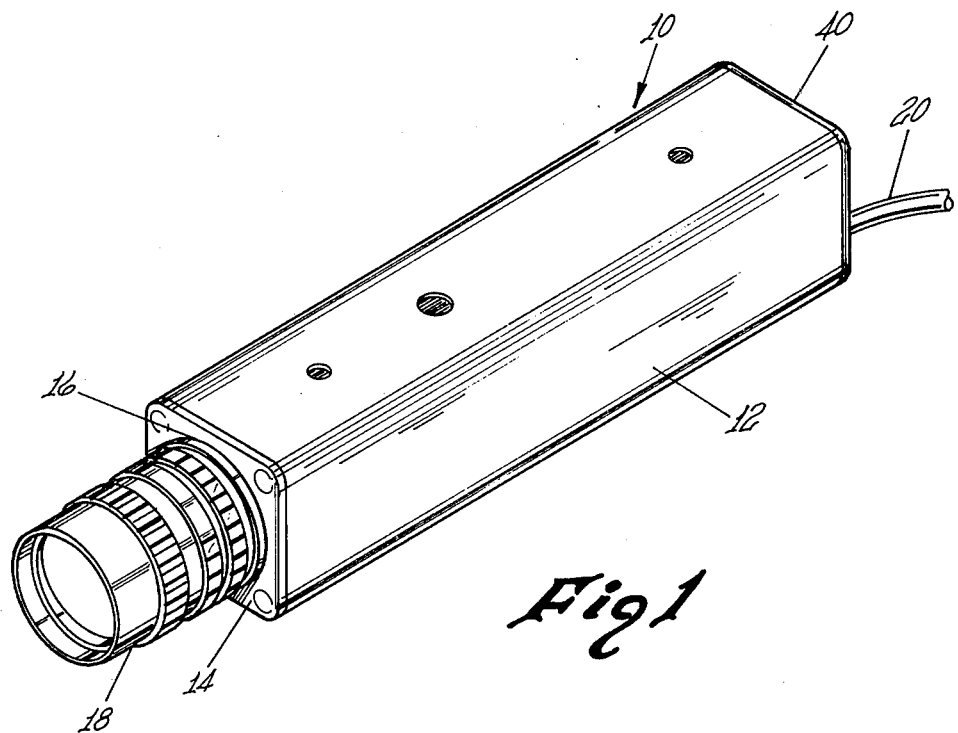
FIG. 1 is an isometric view of a vidicon camera of the present invention.

The preferred embodiment uses a very small camera tube having a photosensitive target plate and an electron gun. This is generally referred to as a vidicon tube or vidicon camera. However, in the broadest aspect of the invention, any small camera tube having a photosensitive surface may be used. Examples of such camera tubes are those having a photoconductive surface or a photoemissive surface. The term video camera tube is meant to broadly cover any such tube. Thus, in FIG. 1 the preferred embodiment depicts a vidicon camera 10 adapted for use in a direct wire or closed circuit television system. The vidicon camera 10 includes a metal housing 12 which, in this embodiment, has dimensions of about 8 inches (20.52cm) in length, 2 inches (5.12 cm) in height and 2 inches (5.12 cm) in width. The housing 12 has a fixed surface 14 which includes means for defining an opening therethrough such as, for example, opening 16. Opening 16 enables an optical image to pass from the exterior of the housing and onto the imaging surface of a vidicon tube enclosed within the housing. A lens 18 is mounted on the housing and is positioned in axial alignment with the opening of the housing and the imaging surface of the vidicon tube. The lens 18 functions to focus an optical image onto the imaging surface of a vidicon tube. A cable 20 extending from housing 12 includes coaxial cable and a polarity of other connectors which are connected to a remotely located television system.

Figure 2:
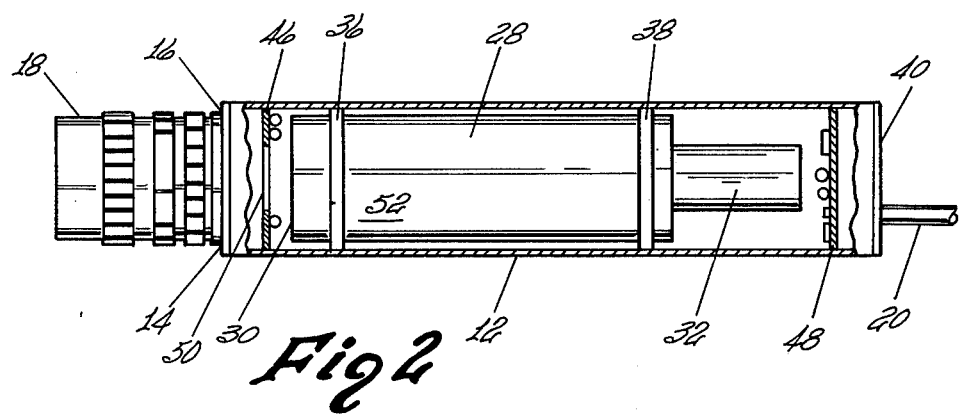
FIG. 2 is a top cross-sectional view of a vidicon camera showing the vidicon tube and printed circuit boards enclosed by a metal housing.

FIG. 2 illustrates in detail the construction of the colored vidicon camera of the present invention. The housing 12 is formed of a metal such as sheet metal which performs two functions; namely (i) to enclose the components within the housing which providing mechanical protection thereto; and (ii) as an electrical shield for spurious external electrical signals. The vidicon camera 10 includes a vidicon tube 28 having an imaging surface 30 at one end thereof and a means for generating electronic beam 32 which is positioned at the end opposite to that of the imaging surface.

The vidicon tube 28 is a small, compact video tube of relatively simple construction. There are a number of types of vidicon tubes manufactured and the type to be selected for use in the vidicon camera is a function of the desired application. Certain types of vidicon tubes are used for high quality pictures for television films for commercial broadcasting. Another known vidicon camera tube has very high sensitivity for internal usage in direct wire or colored television systems. Such applicatons would include a television microscope system. Ruggedized versions of vidicon cameras are utilized in satellite and military applications which require large optical lenses for focusing an optical image onto the imaging surface of the vidicon tube. The imaging surface of the vidicon tube is a photo-sensitive multilayer target. When an optical image is focused on the photo-sensitive target, it produces a charged image which is then scanned by the electronic beam produced by an electron gun 32. Each point on the charge image has a different electrical potential which is responsive to the electronics from the scanning electronic beam, from electron gun 32 to produce an electrical signal therefrom which is a composite video signal having chromance signals representing the optical image.

The housing 12 if formed of metal which shields the vidicon tube 28 and protects the vidicon camera 12. The vidicon tube 28 is held rigidly within the housing 12 by supports 36 and 38. The housing 12 has a front surface 14 and rear surface 40. The front surface 14 defines an opening of a selected dimension and cross-sectional area, such as opening 16. The lens 18 is mounted on the housing 12, specifically on surface 14, such that the lens is in spaced axial alignment with the opening 16 of the housing 12. The imaging surface 30 of the vidicon tube 28 is spaced a predetermined distance from the surface 14 and is in axial alignment with the opening 16. The lens 18 focus an optical image on the imaging surface 30. The size of the opening 16 is selected to be about the dimension of the lens 18 and of a size to pass the optical image onto the imaging surface 30.

In order to facilitate the small compact size and weight of the vidicon camera 10, the minimum control electronics and coils are retained on the housing 12. The circuitry is selectively arranged between a first printed circuit board 46 and a second printed circuit board 48.

The first printed circuit board 46 has cross-sectional area substantially equal to the cross-sectional area of housing 12 and having an aperture 50 of sufficient size to permit the lens 18 to focus an optical image onto the imaging surface 30. In the preferred embodiment, the cross-sectional area of aperture 50 is of a dimension substantially equal to that of the opening 16.

The first printed circuit board is positioned in the housing 12 between the front surface 14 and the imaging surface 30 with the aperture 50 in axial alignment with opening 16.

The second printed circuit board 48 has a cross-sectional area substantially equal to the cross-sectional area of the housing 12 and is positioned between the electron gun 32 end of the vidicon tube 28 and second surface 40. The deflection and focusing coils, generally designated 52, are positioned around the vidicon tube 28. A cable 20 is supported by second surface 40 is electrically connected to the first printed circuit board 46, the second printed circuit board 48 and the coils 52.

Figure 3:
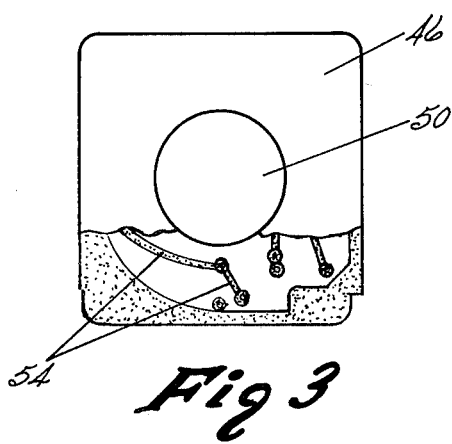
FIG. 3 is a planar view of the first printed circuit board having an aperture formed therethrough, which first printed circuit board is located between the imaging surface of the vidicon tube and an opening formed in the housing.

The first printed circuit board 46 is shown in FIG. 3. The electrical conductor 54 from the conductors for that portion of the circuitry shown in the schematic design of FIG. 5 by dashed line 62. The electrical conductors 54 are formed around the aperture 50. The circuitry included on the first printed circuit board 46 is a high frequency filter and preamplifier circuitry.

Figure 4:
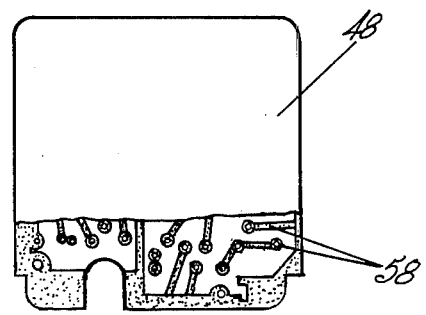
FIG. 4 is a planar view of a second printed circuit board which is located between the end of the vidicon tube opposite the imaging surface and the housing.
Figure 5:
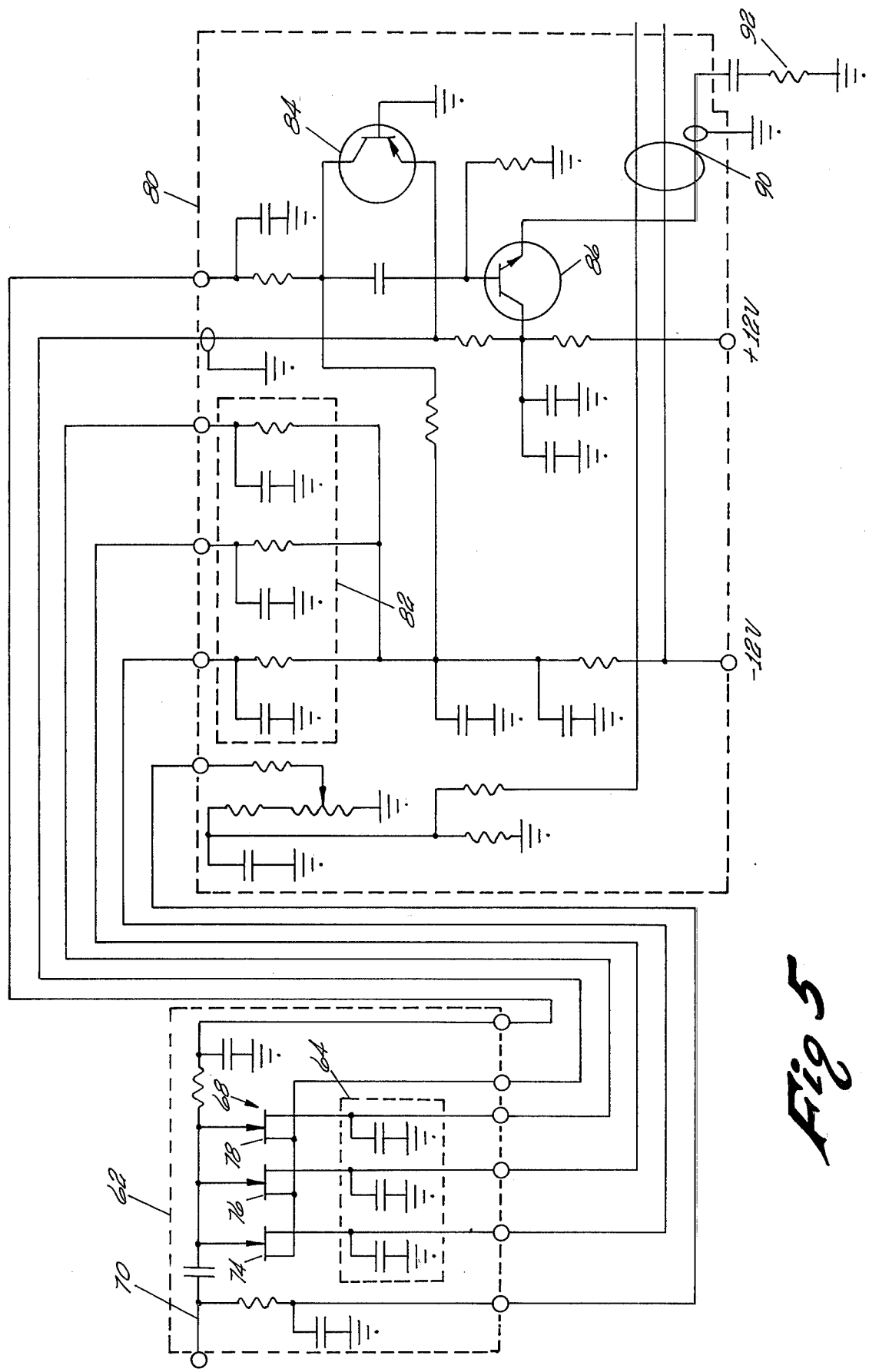
FIG. 5 is a schematic diagram of the electrical circuitry of the vidicon tube, the first printed circuit board, the second printed circuit board and the electrical conductors to a remote television system.

The second printed circuit board 48 is shown in FIG. 4 and is a planar surface supporting electrical conductor 58 defining the conductors for that portion of the circuitry shown in the schematic diagram of FIG. 5 by dashed lines 80.

The circuitry included in the second printed circuit board 48 is an amplifier means and an emitter follower amplifier.

Referring to FIG. 5, the circuitry included on the first printed circuit board of FIGS. 2 and 3 is shown by dashed lines 62. The circuitry includes a high frequency filter 64 for removing signals having a frequency in excess of 6 to 8 megahertz or higher. A preamplifier, generally designated as 68, is electrically connected via a conductor 70 to the vidicon tube 28 to receive therefrom the composite video signal. The preamplifier 68 has a plurality of amplifier stages, stages 74, 76 and 78, electrically connected in parallel to each other and in parallel to the high frequency filter 64. The output signal from the preamplifier is an amplified in phase additive composite signal having the random noise removed therefrom. Each amplifier state is a field effect transistor.

The circuitry included in the second printed circuit board 48 includes a low frequency filter 82, a single state amplifier 84 and an emitter follower amplifier 86. The amplifier 84 amplifies in phase the composite video signal with a predetermined gain. In the embodiment of FIG. 5, the amplifier is a PNP transistor.

The emitter follower amplifier 86 is electrically connected to amplifier 84 and is adapted to drive a coaxial cable 90 with the amplified composite video signal.

In the embodiment of FIG. 5, the emitter follower amplifier is an NPN transistor connected to receive a signal from the PNP transistor connected as a grounded base amplifier. The length of the coaxial cable is about 20 feet and the characteristic impedance is in the order of about 50 to about 75 ohms. Likewise a coaxial cable 90 terminates in a resistor 92 having a matched impedance of the same magnitude as the characteristic impedance of the cable. The coaxial cable 90 enables the vidicon camera 10 to be remotely separated from a video processor.

The remaining conductors required for the voltage source and other electronics such as the control electronics for the deflection and focusing coils and other components normally utilized in a closed circuit television system. are included with the coaxial cable 90 in cable 20 shown in FIGS. 1 and 2.

What is claimed is:

1. A video camera head for use in a direct wire television system comprising a video camera tube having an imaging surface for receiving an optical image thereon and for generating a composite video signal representing a said optical image;

a metal housing having means defining an opening therethrough enabling a said optical image to impinge on said imaging surface, said housing enclosing and supporting said vidicon tube with the imaging surface thereof spaced in axial alignment a predetermined distance from the opening;

a first printed circuit board having an aperture extending axially therethrough of a dimension substantially equal to said opening, said first printed circuit board being positioned in said housing between said opening and said imaging surface with said aperture in axial alignment with said opening and said imaging surface, said first printed circuit board including preamplifier means electrically connected to said vidicon tube for receiving said composite video signal and for producing an amplified additive composite video signal therefrom;

a second printed circuit board positioned between the end of the vidicon tube opposite to and in axial alignment with said imaging surface and said housing, said second printed circuit board including amplifier means for amplifying in phase the composite video signal with a predetermined gain;

emitter follower amplifier means electrically connected to said amplifier means and adapted to drive a coaxial cable with said amplified composite video signal; and conductor means electrically connected between said vidicon tube, said first printed circuit board, said second printed circuit board and a video processor.

2. The vidicon camera of claim 1 wherein said preamplifier includes three parallel stages.

3. The vidicon camera of claim 2 wherein each preamplifier state is a field effect transistor.

4. The vidicon camera of claim 2 further comprising a lens mounted in said means defining said opening and in axial alignment with the imaging surface of said vidicon tube for directing a said optical image on said imaging surface.

5. The vidicon camera of claim 4 wherein the emitter follower amplifier means driving impedance is about 75 ohms.

6. The vidicon camera of claim 5 wherein said conductor means comprises a coaxial cable and wherein the matched coaxial cable impedance is about 75 ohms.

7. The vidicon camera of claim 6 wherein the coaxial cable is selected of a length enabling said vidicon camera to be separated from a television system by up to twenty feet and the driving impedance of said amplifier cable, the cable impedance and termination impedance at the other end of the coaxial cable is matched to produce an amplified composite video signal having an amplitude of a magnitude function as an input to a television system directly connected to the other end of said coaxial cable.

8. A color vidicon camera capable of being connected by a coaxial cable to a remote television system comprising a vidicon tube having an imaging surface of a selected dimension for receiving an optical image thereon and for generating a composite video signal having a chromance signals representing said optical image, said vidicon tube including horizontal and vertical deflection means and focusing means integral therewith;

a metal housing having one surface thereof defining an opening therethrough of a selected dimension and a selected cross-sectional area, said housing enclosing and supporting said vidicon tube with the imaging surface thereof spaced a predetermined distance from the one surface and in axial alignment with the opening;

a lens mounted in said housing and positioned in spaced axial alignment with the opening of the housing and imaging surface of the vidicon tube for focusing a said optical image on said imaging surface;

a first printed circuit board having a cross-sectional area substantially equal to said selected cross-sectional area and having an aperture extending axially therethrough and of a dimension substantially equal to said selected dimension, said first printed circuit board being positioned in said housing between said one surface and said imaging surface with said aperture in axial alignment with said opening and said imaging surface, said first printed circuit board including a high frequency filter, a preamplifier electrically connected to said vidicon tube for receiving said composite video signal, said preamplifier having a plurality of amplifier stages electrically connected in parallel to each other and in parallel to said high frequency filter for producing an amplified in-phase additive composite video signal having a random noise removed therefrom;

a second printed circuit board having a cross-sectional area substantially equal to said selected cross-sectional area, said second printed circuit board being positioned between the end of the vidicon tube opposite to and in axial alignment with said imaging surface and said housing, said second printed circuit board including a low frequency filter;

a single stage amplifier for amplifying in phase the composite video signal with a predetermined gain;

an emitter follower amplifier electrically connected to said single state amplifier and adapted to drive a coaxial cable with said amplified composite video signal; and conductor means electrically connected between said vidicon tube, said first printed circuit board, said second printed circuit board and a television system including connecting said low frequency filter in parallel to said high frequency filter and said single stage amplifier to said preamplifier.

9. The color vidicon camera of claim 8 wherein said preamplifier includes three parallel stages.

10. The color vidicon camera of claim 8 wherein said high frequency filter removes spurious signals having a frequency of about 6 megahertz or higher.

11. The color vidicon camera of claim 8 wherein the single stage amplifier is a single PNP transistor.

12. The color vidicon camera of claim 8 wherein the emitter follower amplifier is a single NPN transistor.

13. The color vidicon camera of claim 9 wherein each preamplifier state is a field effect transistor.

14. The color vidicon camera of claim 11 wherein the PNP transistor is connected as a grounded base amplifier.

15. The color vidicon camera of claim 13 wherein the NPN transistor driving impedance is about 75 ohms.

16. The color vidicon camera of claim 15 wherein said conductor means comprises a coaxial cable and wherein the matched coaxial cable impedance is about 75 ohms.

17. The color vidicon camera of claim 9 wherein the coaxial cable is selected of a length enabling said vidicon camera to be separated from a television system by up to 20 feet and the output of said NPN transistor is applied to the coaxial cable.

* * * * *